(12) United States Patent
Goutopoulos et al.

(10) Patent No.: US 8,802,703 B2
(45) Date of Patent: Aug. 12, 2014

(54) ARYLAMINO N-HETERARYL COMPOUNDS AS MEK INHIBITORS

(75) Inventors: Andreas Goutopoulos, Boston, MA (US); Benny C. Askew, Jr., Marshfield, MA (US); Nhut Kiet Diep, Hauppauge, NY (US); Srinivasa R. Karra, Pembroke, MA (US); Matthias Schwarz, Gland (CH); Henry Yu, Wellesley, MA (US)

(73) Assignee: Merck Serono S.A., Coinsins, Vaud (CH)

( * ) Notice: Subject to any disclaimer, the term of this patent is extended or adjusted under 35 U.S.C. 154(b) by 145 days.

(21) Appl. No.: 12/815,071

(22) Filed: Jun. 14, 2010

(65) Prior Publication Data

US 2010/0256149 A1 Oct. 7, 2010

Related U.S. Application Data

(62) Division of application No. 11/788,028, filed on Apr. 18, 2007, now Pat. No. 7,772,233.

(60) Provisional application No. 60/793,072, filed on Apr. 19, 2006.

(51) Int. Cl.
| | |
|---|---|
| A61K 31/465 | (2006.01) |
| A61K 31/4412 | (2006.01) |
| A61K 31/44 | (2006.01) |
| C07D 213/81 | (2006.01) |
| C07D 213/80 | (2006.01) |
| C07D 213/82 | (2006.01) |
| C07D 405/12 | (2006.01) |
| C07D 213/84 | (2006.01) |
| C07D 237/24 | (2006.01) |
| C07D 213/79 | (2006.01) |
| A61P 35/00 | (2006.01) |
| A61P 29/00 | (2006.01) |

(52) U.S. Cl.
CPC ............ *C07D 213/84* (2013.01); *C07D 213/81* (2013.01); *C07D 213/80* (2013.01); *C07D 213/82* (2013.01); *C07D 405/12* (2013.01); *C07D 237/24* (2013.01); *C07D 213/79* (2013.01)
USPC .......................................... 514/344; 514/352

(58) Field of Classification Search
USPC .......................................... 514/247, 344, 352
See application file for complete search history.

(56) References Cited

U.S. PATENT DOCUMENTS

| 4,144,341 A | 3/1979 | Clark et al. |
| 4,740,511 A | 4/1988 | Blythin |
| 2005/0032846 A1 | 2/2005 | Chen |
| 2005/0250782 A1 | 11/2005 | Marlow et al. |
| 2007/0287737 A1 | 12/2007 | Goutopoulos et al. |
| 2009/0093462 A1 | 4/2009 | Abel et al. |

FOREIGN PATENT DOCUMENTS

| DE | 204480 A1 | 11/1983 |
| EP | 0232659 A1 | 8/1987 |
| GB | 2204040 A | 11/1998 |
| JP | 11292720 | 10/1999 |
| WO | 00/42029 A1 | 7/2000 |
| WO | 2004/052280 A2 | 6/2004 |
| WO | 2004/056789 A1 | 7/2004 |
| WO | 2005/000818 A1 | 6/2005 |
| WO | 2005/051301 A2 | 6/2005 |

OTHER PUBLICATIONS

Spreafico, et al., Clin. Cancer Res.; 19(15) Aug. 1, 2013.*
Sukhvinder, et al., Cancer Research: Apr. 15, 2013; vol. 73, #8, Suppl. 1.*
Clinical Trial of PD-325901, Jul. 2013.*
National Cancer Institute, Jun. 24, 2013.*
Chang, et al., "Signal Transduction Mediated by the Ras/Raf/MEK/ERK pathway from Cytokine Receptors to Transcription Factors: Potential Targeting for Therapeutic Intervention," MTT Leukemia, 2003, 1263-1293, vol. 17.
Crews, et al., "The Primary Structure of MEK, a Protein Kinase that Phosphorylates the ERK Gene Product," Science, 1992, 478-480, vol. 258.
Guo, Z., et al., "Design and Synthesis of Tricyclic Imidazo[4,5-b]pyridin-2-ones as Corticotropin-Releasing Factor-1 Antagonists," Journal of Medicinal Chemistry, 2005, 5104-5107, vol. 48(16).

(Continued)

*Primary Examiner* — James O Wilson
*Assistant Examiner* — Cecilia M Jaisle
(74) *Attorney, Agent, or Firm* — EMD Serono Research & Development Institute; Thomas W. Brown

(57) ABSTRACT

The invention provides novel arylamino N-heteroaryl MEK inhibitors of Formula (I):

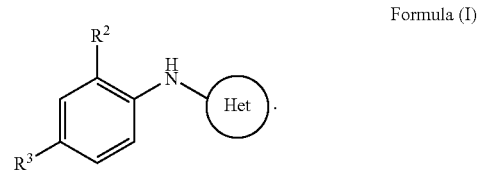

Formula (I)

Such compounds are MEK inhibitors that are useful in the treatment of hyperproliferative diseases, such as cancer and inflammation. Also disclosed is the treatment of a hyperproliferative disease in mammals, and pharmaceutical compositions containing such compounds.

1 Claim, No Drawings

(56) References Cited

OTHER PUBLICATIONS

Kamal, A., et al., "Synthesis of a New Class of 2-anilino Substituted Nicotinyl Arylsulfonylhydrazides as Potential Anticancer and Antibacterial Agents," Bioorganic & Medicinal Chemistry, 2007, 1004-1013, vol. 15(2).

Lee, et al., "Regulation of Hepatocyte Growth Factor-Mediated Urokinase Plasminogen Activator Secretion by MEKIERK Activation in Human Stomach Cancer Cell Lines," Experimental and Molecular Medicine, 2006, 27-35, vol. 38.

Reddy, et al., "Role of MAP Kinase in Tumor Progression and Invasion," Cancer and Metastasis Reviews, 2003, 395-403, vol. 22.

Sherlock, M., et al., "Antiallergy Agents. 1. Substituted 1,8-Naphthyridin-2(1H)-ones as Inhibitors of SRS-A Release," Journal of Medicinal Chemistry, 1988, 2108-2121, vol. 31(11).

Urbanska, H., et al., "Synthesis and Pharmacological Properties of Some Aminoalkyl Esters of Nicotinic Acid Derivatives," Acta Poloniae Pharmaceutica, 1979, 657-665, 36(6).

Friday, Bret B., et al., Advances in Targeting the Ras/Raf/MEK/Erk Mitogen-Activated Protein Kinase Cascade with MEK Inhibitors for Cancer Therapy, Clinical Cancer Research, 2008, pp. 342-346, vol. 14.

Marlow, Allison, L., MEK Inhibitors for the Treatment of Inflammatory Diseases, Array BioPharma, American Chemical Society National Meeting Presentation, Washington, D.C., Aug. 2009, pp. 1-30.

Sebolt-Leopold, Judith S., et al., Blockade of the MAP kinase pathway suppresses growth of colon tumors in vivo, Nature Medicine, 1999, pp. 810-816, vol. 5, No. 7.

\* cited by examiner

ARYLAMINO N-HETERARYL COMPOUNDS AS MEK INHIBITORS

RELATED APPLICATIONS

This application claims the benefit of U.S. Provisional Application No. 60/793,072, filed Apr. 19, 2006, the entire teachings of which are incorporated herein by reference.

FIELD OF THE INVENTION

The invention relates to novel arylamino N-heteroaryl MEK inhibitors, which are useful in the treatment of hyperproliferative diseases, such as cancer and inflammation in mammals. The invention also relates to a method of treating a mammal suffering from, or susceptible to a hyperproliferative disease, such as cancer and inflammation, comprising administering a therapeutically effective amount of an arylamino N-heteroaryl according to the invention. Furthermore, the invention relates to pharmaceutical compositions containing such MEK inhibitors.

BACKGROUND OF THE INVENTION

The Ras/Raf/MEK/MAPK cascade is one of the major pathways transmitting signals from the cell surface to the nucleus. The Ras family of G-proteins relay signals from activated growth factor receptors to the downstream intracellular Raf family kinases, which, in turn, trigger the activation of MEK1 and MEK2 extracellular signal-regulated kinase (ERK1/ERK2) pathway. The MEK family of genes consists of five genes: MEK1, MEK2, MEK3, MEK4 and MEK5. The structure of MEK consists of an amino-terminal negative regulatory domain and a carboxy-terminal MAP kinase-binding domain, which is necessary for binding and activation of ERKs. MEK1 is a 393-amino-acid protein with a molecular weight of 44 kDa (Crews, et al., 258 SCIENCE 478-80 (1992)).

Upstream and downstream signalling of the Ras/Raf/ MEK/MAPK cascade involves multiple pathways, however MEK appears to specifically phosphorylate MAPK. The role of MAPK in cancer (Reddy, et al., 22 CANCER METASTASIS REV. 395-403 (2004)), and the dysfunctional activation of signalling components in the MAPK pathway in a high proportion of tumor types, has lead to an extended interest in MEK as a cancer target and the development of MEK inhibitors (Chang et al., 17 LEUKEMIA 1263-93 (2003); Lee, et al., 38 EXP. MOL. MED. 27-35 (2006)).

Among the furthest advanced MEK inhibitors is Pfizer's PD-0325901, a diarylamine derived MEK inhibitor, that has recently entered phase II clinical trials for the potential oral treatment of cancer.

Array Biopharma's ARRY142886, a phenylamino-2-pyridone derived MEK inhibitor, is currently in Phase I clinical trials.

WO 00/42029 (Warner-Lambert Company) further reports about diarylamines (A) that exhibit MEK inhibitory activity and are potentially useful for the treatment of cancer and other proliferative diseases.

(A)

WO 04/056789 (Warner-Lambert Company) reports about oxadiazole- and thiadiazole-phenylamine derivatives (B) as MEK inhibitors for the potential treatment of inflammation and proliferative diseases.

(B)

WO 05/051301 (Array Biopharma Inc.) relates to heterocyclic compounds (C), which are MEK inhibitors and useful for the potential treatment of hyperproliferative diseases.

(C)

WO 05/000818 (Warner-Lambert Company) relates to phenylamino-2-pyridone derivatives (D) as MEK inhibitors that might be useful for the treatment of proliferative diseases.

(D)

SUMMARY OF THE INVENTION

The invention provides in one aspect MEK inhibitors according to Formula (I). These compounds are suitable for the treatment of hyperproliferative diseases such as cancer and inflammation.

It is another aspect of the present invention to provide MEK inhibitors according to Formula (I), which are able to downregulate, especially inhibit the activity or function of MEK especially in mammals.

It is another aspect of the present invention to provide a method for treating a mammal suffering from or susceptible to a hyperproliferative disease, comprising administering to the mammal a therapeutically effective amount of a MEK inhibitor according to Formula (I). Said diseases include cancer and inflammation.

It is furthermore an aspect of the present invention to provide a MEK inhibitor according to Formula (I) for use as a medicament.

It is furthermore an aspect of the present invention to provide a MEK inhibitor according to Formula (I) for the preparation of a medicament for the treatment of a hyperproliferative disease.

It is furthermore an aspect of the present invention to provide a pharmaceutical formulation, which comprises a MEK inhibitor according to Formula (I) and a pharmaceutically acceptable carrier.

It is finally an aspect of the present invention to provide a process for making compounds according to Formula (I).

MEK inhibitors of the invention have the following general formula:

Formula (I)

wherein $R^1$, $R^2$ and Het are as defined in the detailed description.

DETAILED DESCRIPTION OF THE INVENTION

One aspect of the present invention to provide novel compounds according to Formula (I) that are useful in the treatment of hyperproliferative diseases. Specifically, hyperproliferative diseases related to the hyperactivity of MEK as well as diseases associated to MEK, such as cancer and inflammation in mammals.

As a result, this invention provides in a first aspect, novel compounds as well as pharmaceutically acceptable salts and pharmaceutically active derivatives thereof, that are useful for the treatment of hyperproliferative diseases, such as cancer and inflammation.

The compounds are defined by Formula (I):

Formula (I)

as well as pharmaceutically acceptable salts and pharmaceutically active derivatives thereof, wherein:
Het is selected from wherein * is the connecting position;
W is selected from: 1) heteroaryl containing 1-4 heteroatoms or heterocycloalkyl containing 1-4 heteroatoms, each of which is optionally substituted with 1 to 5 substituents $R^{11}$; and 2) is aryl, halogen, $C_1$-$C_{10}$-alkyl-$OR^6$, $C_1$-$C_{10}$-alkyl-$NR^7R^8$, —C=$NNR^6R^7$, —C=$NOR^7$, $C_1$-$C_{10}$ alkyl($NR^7$)($NR^7R^8$), —C(O)$R^6$, —C(O)$OR^6$, —C(O)$NR^7R^8$, —C(O)$NR^7OR^6$, —C(O)($C_3$-$C_{10}$ cycloalkyl), —C(O)($C_1$-$C_{10}$ alkyl), —C(O)(aryl), —C(O)$NR^7$($C_1$-$C_{10}$ alkyl)heterocycloalkyl, —C(O)(heteroaryl), —C(O)(heterocycloalkyl), —CN, —C(O)$NR^7NR^8R^6$, —C(O)C(O)$R^6$, —C(O)$CR^6R^7$C(O)$R^8$, —$NR^7R^8$, —$NR^7C(O)R^8$, —$NRC(O)NR^7R^8$ or —C(O)$NR^7NR^8C(O)R^6$.

$R^1$ and $R^9$ are independently selected from hydrogen, halogen, cyano, azido, $C_1$-$C_6$ alkyl, $C_1$-$C_6$ alkoxy, $C_3$-$C_{10}$ cycloalkyl, aryl, heteroaryl, heterocycloalkyl, $C_1$-$C_4$ alkyl-C(O)$OR^6$, $C_1$-$C_4$ alkyl-$OR^6$, $C_1$-$C_4$ alkyl-C(O)$NR^7R^8$, —C(O)$OR^6$, —C(O)$R^6$, —$NR^7C(O)OR^6$, —OC(O)$R^6$, —$NR^7R^8$, —$SR^6$ and —$NR^7S(O)_2R^6$, wherein said alkyl, aryl, heteroaryl and heterocycloalkyl are substituted or unsubstituted.

$R^2$ and $R^3$ are independently halogen.

$R^4$ and $R^5$ are independently selected from hydrogen, halogen, $C_1$-$C_6$ alkyl and $C_1$-$C_6$ alkoxy, wherein said alkyl or alkoxy is substituted or unsubstituted.

$R^6$, $R^7$ and $R^8$ are independently selected from hydrogen, $C_1$-$C_{10}$ alkyl, $C_3$-$C_{10}$ cycloalkyl, aryl, arylalkyl, heteroaryl, or heterocycloalkyl, $C_1$-$C_4$ alkyl-C(O)OR', $C_1$-$C_4$ alkyl-OR', $C_1$-$C_4$ alkyl-hetercylcoalkyl, $C_1$-$C_4$ alkyl-diol, and $C_1$-$C_4$ alkyl-C(O)NR'R", wherein said alkyl, cycloalkyl, aryl, heteroaryl and heterocycloalkyl are substituted or unsubstituted; or $R^7$ and $R^8$ can be taken together with the atom to which they are attached to form a 4 to 10 membered heteroaryl or heterocycloalkyl ring, which are independently substituted or unsubstituted. Additionally, $R^6$, $R^7$ and $R^8$ can each independently be $C_1$-$C_4$ alkyl-hetercylcoalkyl or C1-C4 alkyl-diol.

$R^{10}$ is selected from hydrogen, halogen and $C_1$-$C_6$ alkyl; wherein said alkyl is substituted or unsubstituted.

$R^{11}$ is selected from: hydrogen, $C_1$-$C_6$-alkyl, —$OR^6$, —$NR^7R^8$, —$SR^6$ and —$NR^7S(O)_2R'$.

R' and R" are independently selected from hydrogen, $C_1$-$C_6$-alkyl or aryl, wherein said alkyl or aryl is substituted or unsubstituted.

In preferred aspects, the variables have the following meanings:
W is selected from 1) heteroaryl containing 1-4 heteroatoms which is optionally substituted by 1 to 5 substituents, $R^{11}$; and 2) aryl, $C_1$-$C_{10}$-alkyl-$OR^6$, $C_1$-$C_{10}$-alkyl-$NR^7R^8$, —C=$NNR^7R^8$, —C=$NOR^7$, $C_1$-$C_{10}$ alkyl($NR^7$)($NR^7R^8$), —C(O)$R^6$, —C(O)$OR^6$, —C(O)$NR^7R^6$, —C(O)$NR^7OR^6$, —C(O)($C_3$-$C_{10}$ cycloalkyl), —C(O)($C_1$-$C_{10}$ alkyl), —C(O)(aryl), —C(O)$NR^7$($C_1$-$C_{10}$ alkyl)heterocycloalkyl, —C(O)(heteroaryl), —C(O)(heterocyclyl), —CN, —C(O)$NR^7NR^8R^6$, —C(O)C(O)$R^6$, —C(O)$CR^6R^7C(O)R^8$, —$NR^7R^8$, —$NR^7C(O)R^8$, —$NRC(O)NR^7R^8$, or —C(O)$NR^7NR^8C(O)R^6$. When W is heteroaryl, said heteraryl is preferably oxadiazole, which is optionally substituted by 1-3 $R^{11}$ substituents. Particular embodiments of W also include —C(O)OR⁶, —C(O)NR⁷R⁶, —C(O)NR⁷OR⁶, —C(O)NR⁷ (C₁-C₁₀ alkyl)heterocycloalkyl and —CN.

R¹ is selected from halogen, cyano, azido, C₁-C₆ alkyl, C₁-C₆ alkoxy, C₃-C₁₀ cycloalkyl, aryl, heteroaryl, heterocycloalkyl, C₁-C₄ alkyl-C(O)OR⁶, C₁-C₄ alkyl-OR⁶, C₁-C₄ alkyl-C(O)NR⁷R⁸, —C(O)OR⁶, —C(O)R⁶, —NR⁷C(O) OR⁶, —OC(O)R⁶, —NR⁷R⁸, —SR⁶ and —NR⁷S(O)₂R⁶, wherein said alkyl, aryl, heteroaryl or heterocycloalkyl is substituted or unsubstituted. In a particular embodiment, R¹ is halogen, C₁-C₆ alkoxy or —NR⁷R⁸.

R² is selected from F, Cl, I, Br. In a particular embodiment, R² is F.

R³ is selected from F, Cl, I. In a particular embodiment, R³ is I.

R⁴ and R⁵ are independently either hydrogen or C₁-C₆ alkyl. In a particular embodiment, R⁴ and R⁵ are each hydrogen.

R⁶, R⁷ and R⁸ are independently selected from hydrogen, C₁-C₁₀ alkyl, C₁-C₄ alkyl-C(O)OR', C₁-C₄ alkyl-OR', C₁-C₄ alkyl-C(O)NR'R", wherein said alkyl is substituted or unsubstituted; or R⁷ and R⁸ can be taken together with the atom to which they are attached to form a 6 membered heterocycloalkyl ring with 1 or 2 nitrogen atoms and optionally an oxygen atom, which is substituted or unsubstituted. In another aspect of the invention, R⁶, R⁷ and R⁸ can each independently be C₁-C₄ alkyl-hetercylcoalkyl, or C₁-C₄ alkyl-diol, in addition to the values just described. In a particular embodiment, said heterocycloalkyl is morpholinyl, piperidinyl, 2,2-dimethyl-1,3-dioxolane, or piperazinyl.

R⁹ is selected from hydrogen, halogen, C₁-C₁₀ alkyl, C₁-C₄ alkoxy. In a particular embodiment, R⁹ is hydrogen.

R¹⁰ is selected from Cl, I, F, or Br. In a particular embodiment, R¹⁰ is F.

R¹¹ is selected from —OR⁶, —NR⁷R⁸, —SR⁶ and —NR⁷S (O)₂R'.

R' and R" are independently either hydrogen, or C₁-C₆-alkyl.

As set forth above, the variables R¹, R⁴, R⁵, R⁶, R⁷, R⁸, R⁹, R¹⁰, R¹¹, R' and R" are optionally substituted. In this case they are independently substituted with 1 to 5, preferably 1 to 3, more preferably 1 or 2 groups, independently selected from halogen, cyano, nitro, —CF₃, —CHF, —CHF, —OCF₃, —OCHF₂, —OCH₂F, —SCF₃, —SCHF₂, —SCH₂F, azido, amino, aminosulfonyl, sulfonylamine, sulfanyl, sulfonyl, sulfinyl, sulfonyloxy, acyl, acyloxy, carboxy, alkoxy or hydroxyl. In another aspect of the invention, the variables just described can each independently be substituted with C₁-C₄ alkyl-hetercylcoalkyl, in addition to the values just described. In a particular embodiment, the optional substituents are halogen, cyano, nitro, alkoxy, hydroxyl, —CF₃, —CHF₂, —CHF, —OCF₃, —OCHF₂, —OCH₂F, —SCF₃, —SCHF₂, —SCH₂F, or azido. In a further particular embodiment, the optional substituents are halogen, cyano, nitro, hydroxyl, —CF₃, —CHF₂, —CH₂F, —OCF₃, —OCHF₂, —OCH₂F, —SCF₃, —SCHF₂, —SCH₂F, —OH, —OCH₃, —NH₂ or —N(CH₃)₂.

In another aspect, the invention provides compounds of the Formula (II):

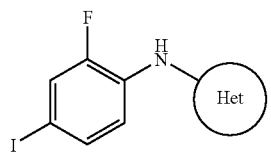

Formula (II)

as well as pharmaceutically acceptable salts and pharmaceutically active derivatives thereof, wherein:

Het is selected from:

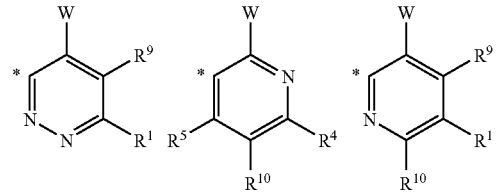

wherein * is the connecting position.

W is selected from 1) heteroaryl containing 1-4 heteroatoms or heterocycloalkyl containing 1-4 heteroatoms each of which is optionally substituted by 1 to 5 substituents R¹¹; and 2) aryl, halogen, C₁-C₁₀-alkyl-OR⁶, C₁-C₁₀-alkyl-NR⁷R⁸, —C=NNR⁶R⁷, —C=NOR⁷, C₁-C₁₀ alkyl(NR⁷)(NR⁷R⁸), —C(O)R⁶, —C(O)OR⁶, —C(O)NR⁷R⁸, —C(O)NR⁷OR⁶, —C(O)(C₃-C₁₀ cycloalkyl), —C(O)(C₁-C₁₀ alkyl), —C(O) (aryl), —C(O)NR⁷(C₁-C₁₀ alkyl)-heterocycloalkyl, —C(O) (heteroaryl), —C(O)(heterocycloalkyl), —CN, —C(O) NR⁷NR⁸R⁶, —C(O)C(O)R⁶, —C(O)CR⁶R⁷C(O)R⁸, —NR⁷R⁸, —NR⁷C(O)R⁸, —NRC(O)NR⁷R⁸ or —C(O) NR⁷NR⁸C(O)R⁶.

R¹ and R⁹ are independently selected from hydrogen, halogen, cyano, azido, C₁-C₆ alkyl, C₁-C₆ alkoxy, C₃-C₁₀ cycloalkyl, aryl, heteroaryl, heterocycloalkyl, C₁-C₄ alkyl-C(O)OR⁶, C₁-C₄ alkyl-OR⁶, C₁-C₄ alkyl-C(O)NR⁷R⁸, —C(O) OR⁶, —C(O)R⁶, —NR⁷C(O)OR⁶, —OC(O)R⁶, —NR⁷R⁸, —SR⁶ or —NR⁷S(O)₂R⁶, wherein said alkyl, aryl, heteroaryl and heterocycloalkyl are substituted or unsubstituted.

R⁴ and R⁵ are independently selected from hydrogen, halogen, C₁-C₆ alkyl or C₁-C₆ alkoxy, wherein said alkyl or alkoxy is substituted or unsubstituted.

R⁶, R⁷ and R⁸ are independently selected from hydrogen, C₁-C₁₀ alkyl, C₃-C₁₀ cycloalkyl, aryl, arylalkyl, heteroaryl, or heterocycloalkyl, C₁-C₄ alkyl-C(O)OR', C₁-C₄ alkyl-OR', C₁-C₄ alkyl-(heterocycloalkyl), C₁-C₄ alkyl-diol, and C₁-C₄ alkyl-C(O)NR'R", wherein said alkyl, cycloalkyl, aryl, heteroaryl and heterocyclyl are substituted or unsubstituted; or R⁷ and R⁸ can be taken together with the atom to which they are attached to form a 4 to 10 membered heteroaryl or heterocycloalkyl ring, each of which is substituted or unsubstituted.

R¹⁰ is selected from hydrogen, halogen and C₁-C₆ alkyl; wherein said alkyl is substituted or unsubstituted.

R¹¹ is selected from hydrogen, C₁-C₆-alkyl, —OR⁶, —NR⁷R⁸, —SR⁶ and —NR⁷S(O)₂R'.

R' and R" are independently selected from hydrogen, C₁-C₆-alkyl or aryl, wherein said alkyl or aryl is substituted or unsubstituted.

In preferred aspects, the variables have the following meanings:

W is selected from 1) heteroaryl containing 1-4 heteroatoms which is optionally substituted by 1 to 5 substituents, R¹¹; or 2) aryl, C₁-C₁₀-alkyl-OR⁶, C₁-C₁₀-alkyl-NR⁷R⁸, —C=NNR⁷R⁸, —C=NOR⁷, C₁-C₁₀ alkyl(NR⁷)(NR⁷R⁸), —C(O)R⁶, —C(O)OR⁶, —C(O)NR⁷R⁶, —C(O)NR⁷OR⁶, —C(O)(C₃-C₁₀ cycloalkyl), —C(O)(C₁-C₁₀ alkyl), —C(O) (aryl), —C(O)NR⁷(C₁-C₁₀ alkyl)heterocycloalkyl, —C(O) (heteroaryl), —C(O)(heterocyclyl), —CN, —C(O) NR⁷NR⁸R⁶, —C(O)C(O)R⁶, —C(O)CR⁶R⁷C(O)R⁸, —NR⁷R⁸, —NR⁷C(O)R⁸, —NRC(O)NR⁷R⁸, or —C(O) NR⁷NR⁸C(O)R⁶. In a particular embodiment, when W is heteroaryl, said heteraryl is preferably oxadiazole, which is optionally substituted by 1-3 substituents, $R^{11}$. In another particular embodiment, W is —C(O)$R^6$, —C(O)N$R^7R^6$, —C(O)N$R^7$O$R^6$, —C(O)N$R^7$($C_1$-$C_{10}$ alkyl)heterocycloalkyl or —CN.

$R^1$ is selected from halogen, cyano, azido, $C_1$-$C_6$ alkyl, $C_1$-$C_6$ alkoxy, $C_3$-$C_{10}$ cycloalkyl, aryl, heteroaryl, heterocycloalkyl, $C_1$-$C_4$ alkyl-C(O)O$R^6$, $C_1$-$C_4$ alkyl-O$R^6$, $C_1$-$C_4$ alkyl-C(O)N$R^7R^8$, —C(O)O$R^6$, —C(O)$R^6$, —N$R^7$C(O)O$R^6$, —OC(O)$R^6$, —N$R^7R^8$, —S$R^6$ or —N$R^7$S(O)$_2R^6$, wherein said alkyl, aryl, heteroaryl and heterocycloalkyl is substituted or unsubstituted. In a particular embodiment, $R^1$ is halogen, $C_1$-$C_6$ alkoxy or —N$R^7R^8$.

$R^2$ is selected from F, Cl, I, Br. In a particular embodiment, $R^2$ is F.

$R^3$ is selected from F, Cl, I. In a particular embodiment, $R^3$ is I.

$R^4$ and $R^5$ are independently hydrogen or $C_1$-$C_6$ alkyl. In a particular embodiment, $R^4$ and $R^5$ are each hydrogen.

$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR', $C_1$-$C_4$ alkyl-(heterocycloalkyl), $C_1$-$C_4$ alkyl-diol, and $C_1$-$C_4$ alkyl-C(O)NR'R", wherein said alkyl is substituted or unsubstituted; or $R^7$ and $R^8$ can be taken together with the atom to which they are attached to form a 6 membered heterocycloalkyl ring with 1 or 2 nitrogen atoms and optionally an oxygen atom, which is substituted or unsubstituted. In a particular embodiment, said heterocycloalkyl ring is morpholinyl, piperidinyl, 2,2-dimethyl-1,3-dioxolane, or piperazinyl.

$R^9$ is selected from hydrogen, halogen, $C_1$-$C_{10}$ alkyl, $C_1$-$C_4$ alkoxy. In a particular embodiment, $R^9$ is hydrogen.

$R^{10}$ is selected from Cl, I, F, and Br. In a particular embodiment, $R^{10}$ is F.

$R^{11}$ is selected from —O$R^6$, —N$R^7R^8$, —S$R^6$ and —N$R^7$S(O)$_2$R'.

R' and R" are independently either hydrogen, $C_1$-$C_6$-alkyl.

As discussed above, $R^1$, $R^5$, $R^6$, $R^7$, $R^8$, $R^9$, $R^{10}$, $R^{11}$, R' and R" are optionally substituted. In this case they are independently substituted as described above.

Particular embodiments of the invention are encompassed by compounds of the Formulae (IIIa), (IIIb), or (IIIc):

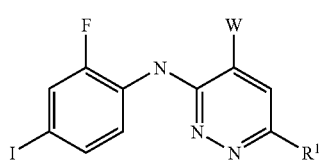

Formula (IIIa)

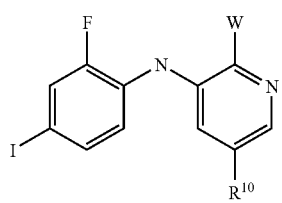

Formula (IIIb)

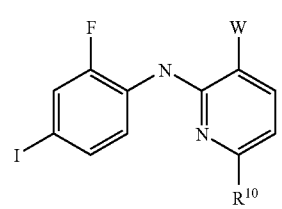

Formula (IIIc)

as well as pharmaceutically acceptable salts and pharmaceutically active derivatives thereof, wherein:

W is selected from 1) heteroaryl containing 1-4 heteroatoms or heterocycloalkyl containing 1-4 heteroatoms each of which is optionally substituted by 1 to 5 substituents, $R^{11}$; and 2) aryl, halogen, $C_1$-$C_{10}$-alkyl-O$R^6$, $C_1$-$C_{10}$-alkyl-N$R^7R^8$, —C=NN$R^6R^7$, —C=NO$R^7$, $C_1$-$C_{10}$ alkyl(N$R^7$)(N$R^7R^8$), —C(O)$R^6$, —C(O)O$R^6$, —C(O)N$R^7R^8$, —C(O)N$R^7$O$R^6$, —C(O)($C_3$-$C_{10}$ cycloalkyl), —C(O)($C_1$-$C_{10}$ alkyl), —C(O)(aryl), —C(O)N$R^7$($C_1$-$C_{10}$ alkyl)heterocycloalkyl, —C(O)(heteroaryl), —C(O)(heterocycloalkyl), —CN, —C(O)N$R^7$N$R^8R^6$, —C(O)C(O)$R^6$, —C(O)C$R^6R^7$C(O)$R^8$, —N$R^7R^8$, —N$R^7$C(O)$R^8$, —NRC(O)N$R^7R^8$ or —C(O)N$R^7$N$R^8$C(O)$R^6$.

$R^1$ is selected from hydrogen, halogen, cyano, azido, $C_1$-$C_6$ alkyl, $C_3$-$C_{10}$ cycloalkyl, aryl, heteroaryl, heterocycloalkyl, $C_1$-$C_4$ alkyl-C(O)O$R^6$, $C_1$-$C_4$ alkyl-O$R^6$, $C_1$-$C_4$ alkyl-C(O)N$R^7R^8$, —C(O)O$R^6$, —C(O)$R^6$, —N$R^7$C(O)O$R^6$, —OC(O)$R^6$, —N$R^7R^8$, —S$R^6$ or —N$R^7$S(O)$_2R^6$, wherein said alkyl, aryl, heteroaryl and heterocycloalkyl is substituted or unsubstituted.

$R^6$, $R^7$ and $R^8$ are independently selected from hydrogen, $C_1$-$C_{10}$ alkyl, $C_3$-$C_{10}$ cycloalkyl, aryl, arylalkyl, heteroaryl, or heterocycloalkyl, $C_1$-$C_4$ alkyl-C(O)OR', $C_1$-$C_4$ alkyl-OR', $C_1$-$C_4$ alkyl-(heterocycloalkyl), $C_1$-$C_4$ alkyl-diol, and $C_1$-$C_4$ alkyl-C(O)NR'R"; wherein said alkyl, cycloalkyl, aryl, heteroaryl and heterocycloalkyl are substituted or unsubstituted; or $R^7$ and $R^8$ can be taken together with the atom to which they are attached to form a 4 to 10 membered heteroaryl or heterocycloalkyl ring, with 1-4 heteroatoms, each ring being substituted or unsubstituted;

$R^{10}$ is selected from hydrogen, halogen or $C_1$-$C_6$ alkyl; wherein said alkyl is substituted or unsubstituted.

$R^{11}$ is selected from hydrogen, $C_1$-$C_6$-alkyl, —O$R^6$, —N$R^7R^8$, —S$R^6$ and —N$R^7$S(O)$_2$R'.

R' and R" are independently selected from hydrogen, $C_1$-$C_6$-alkyl and aryl, wherein said alkyl or aryl is substituted or unsubstituted.

In preferred aspects, the variables have the following meanings:

W is selected from 1) heteroaryl containing 1-4 heteroatoms which is optionally substituted by 1 to 5 substituents, $R^{11}$; or 2)aryl, $C_1$-$C_{10}$-alkyl-O$R^6$, $C_1$-$C_{10}$-alkyl-N$R^7R^8$, —C=NN$R^7R^8$, —C=NO$R^7$, $C_1$-$C_{10}$ alkyl(N$R^7$)(N$R^7R^8$), —C(O)$R^6$, —C(O)O$R^6$, —C(O)N$R^7R^6$, —C(O)N$R^7$O$R^6$, —C(O)($C_3$-$C_{10}$ cycloalkyl), —C(O)($C_1$-$C_{10}$ alkyl), —C(O)(aryl), —C(O)N$R^7$($C_1$-$C_{10}$ alkyl)heterocycloalkyl, —C(O)(heteroaryl), —C(O)(heterocyclyl), —CN, —C(O)N$R^7$N$R^8R^6$, —C(O)C(O)$R^6$, —C(O)C$R^6R^7$C(O)$R^8$, —N$R^7R^8$, —N$R^7$C(O)$R^8$, —NRC(O)N$R^7R^8$, or —C(O)N$R^7$N$R^8$C(O)$R^6$. In a particular embodiment, when W is heteroaryl, said heteraryl is preferably oxadiazole, which is optionally substituted by 1-3 substituents, $R^{11}$. In another particular embodiment, W is —C(O)O$R^6$, —C(O)N$R^7R^6$, —C(O)N$R^7$O$R^6$, —C(O)N$R^7$($C_1$-$C_4$ alkyl)heterocycloalkyl or —CN.

$R^1$ is selected from halogen, cyano, azido, $C_1$-$C_6$ alkyl, $C_1$-$C_6$ alkoxy, $C_3$-$C_{10}$ cycloalkyl, aryl, heteroaryl, heterocycloalkyl, $C_1$-$C_4$ alkyl-C(O)O$R^6$, $C_1$-$C_4$ alkyl-O$R^6$, $C_1$-$C_4$ alkyl-C(O)N$R^7R^8$, —C(O)O$R^6$, —C(O)$R^6$, —N$R^7$C(O)O$R^6$, —OC(O)$R^6$, —N$R^7R^8$, —S$R^6$ or —N$R^7$S(O)$_2R^6$, wherein said alkyl, aryl, heteroaryl and heterocycloalkyl is substituted or unsubstituted. In a particular embodiment, $R^1$ is halogen, $C_1$-$C_6$ alkoxy or —N$R^7R^8$.

$R^2$ is selected from F, Cl, I, Br. In a particular embodiment, $R^2$ is F.

$R^3$ is selected from F, Cl, I. In a preferred embodiment, $R^3$ is I.

$R^6$, $R^7$ and $R^8$ are independently selected from hydrogen, $C_1$-$C_{10}$ alkyl, $C_1$-$C_4$ alkyl-C(O)OR', $C_1$-$C_4$ alkyl-OR', $C_1$-$C_4$ alkyl-(heterocycloalkyl), $C_1$-$C_4$ alkyl-diol and $C_1$-$C_4$ alkyl-C(O)NR'R", wherein said alkyl is substituted or unsubstituted; or $R^7$ and $R^8$ can be taken together with the atom to which they are attached to form a 6 membered heterocycloalkyl ring with 1 or 2 nitrogen atoms and optionally an oxygen atom, which is substituted or unsubstituted; preferably said heterocycloalkyl ring is morpholinyl, piperidinyl or piperazinyl.

$R^{10}$ is selected from Cl, I, F, or Br. In a particular embodiment, $R^{10}$ is F.

$R^{11}$ is selected from $-OR^6$, $-NR^7R^8{}_9$—$SR^6$ or $-NR^7S(O)_2R'$.

R' and R" are independently either hydrogen or $C_1$-$C_6$-alkyl.

$R^1$, $R^5$, $R^6$, $R^7$, $R^8$, $R^9$, $R^{10}$, $R^{11}$, R', and R" are optionally substituted. Values and particular values for optional substituents are as described above.

Compounds according to Formula (I) include in particular those of the group consisting of: 6-Fluoro-2-(2-fluoro-4-iodophenylamino)nicotinic acid; (R)-N-((2,2-dimethyl-1,3-dioxolan-4-yl)methoxy)-6-fluoro-2-(2-fluoro-4-iodophenylamino)nicotinamide; (R)—N-(2,3-dihydroxypropoxy)-6-fluoro-2-(2-fluoro-4-iodophenylamino)nicotinamide; 5-Fluoro-3-(2-fluoro-4-iodo-phenylamino)-pyridine-2-carbonitrile; 5-Fluoro-3-(2-fluoro-4-iodo-phenylamino)-pyridine-2-carboxylic acid; 5-Fluoro-3-(2-fluoro-4-iodo-phenylamino)-pyridine-2-carboxylic acid amide; 6-Chloro-3-(2-fluoro-4-iodo-phenylamino)-pyridazine-4-carboxylic acid; 3-(2-Fluoro-4-iodo-phenylamino)-6-morpholin-4-yl-pyridazine-4-carboxylic acid; 3-(2-Fluoro-4-iodo-phenylamino)-6-methoxy-pyridazine-4-carboxylic acid; 6-Chloro-3-(2-fluoro-4-iodo-phenylamino)-pyridazine-4-carboxylic acid (2,2-dimethyl-[1,3]-dioxolan-4-ylmethoxy)-amide; 6-Chloro-3-(2-fluoro-4-iodo-phenylamino)-pyridazine-4-carboxylic acid amide; and 6-Chloro-3-(2-fluoro-4-iodo-phenylamino)-pyridazine-4-carboxylic acid (2-morpholin-4-yl-ethyl)-amide, or pharmaceutically acceptable salts thereof.

The employed terms have independently the meaning as described below:

"$C_1$-$C_{10}$-alkyl" refers to monovalent alkyl groups having 1 to 10 carbon atoms. This term is exemplified by groups such as methyl, ethyl, n-propyl, isopropyl, n-butyl, isobutyl, tert-butyl, n-hexyl and the like. By analogy, "$C_1$-$C_{12}$-alkyl" refers to monovalent alkyl groups having 1 to 12 carbon atoms, including "$C_1$-$C_6$-alkyl" groups and heptyl, octyl, nonyl, decanoyl, undecanoyl and dodecanoyl groups and "$C_1$-$C_{10}$-alkyl" refers to monovalent alkyl groups having 1 to 10 carbon atoms, "$C_1$-$C_8$-alkyl" refers to monovalent alkyl groups having 1 to 8 carbon atoms and "$C_1$-$C_5$-alkyl" refers to monovalent alkyl groups having 1 to 5 carbon atoms.

"Heteroalkyl" refers to $C_1$-$C_{12}$-alkyl, preferably $C_1$-$C_6$-alkyl, wherein at least one carbon has been replaced by a heteroatom selected from oxygen, nitrogen or sulfur, including 2-methoxy ethyl.

"Aryl" refers to an unsaturated aromatic carbocyclic group of from 6 to 14 carbon atoms having a single ring (e.g., phenyl) or multiple condensed rings (e.g., naphthyl). Examples include phenyl, naphthyl, phenantrenyl and the like.

"$C_1$-$C_6$-alkyl aryl" refers to aryl groups having a $C_1$-$C_6$-alkyl substituent, including methyl phenyl, ethyl phenyl and the like.

"Aryl $C_1$-$C_6$-alkyl" refers to $C_1$-$C_6$-alkyl groups having an aryl substituent, including benzyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazoly-1,1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 1,2,3,4-tetrahydroquinolyl, 1,2,3,4-tetrahydroisoquinolyl, purinyl, pteridinyl, carbazolyl, xanthenyl or benzoquinolyl.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl ($-CH=CH_2$), n-2-propenyl (allyl, $-CH_2CH=CH_2$) and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl ($-C\equiv CH$), propargyl ($-CH_2\equiv CH$), and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Examples of $C_3$-$C_8$-cycloalkyl groups include cyclopentyl, cyclohexyl, norbornyl and the like.

"Heterocycle" refers to a $C_3$-$C_8$-cycloalkyl group according to the definition above, in which up to 3 carbon atoms are replaced by heteroatoms chosen from the group consisting of O, S, or NR, R being defined as hydrogen or methyl. "Heterocycle" can be used interchangeably with "heterocycloalkyl." Examples of heterocycles include pyrrolidine, piperidine, piperazine, morpholine, tetrahydrofuran, 2,2-dimethyl-1,3-dioxolane, and the like.

"Acyl" refers to the group $-C(O)R$, where R includes "$C_1$-$C_{12}$-alkyl", "$C_1$-$C_6$-alkyl", "aryl", "heteroaryl", "$C_3$-$C_8$-cycloalkyl", "heterocycloalkyl", "aryl $C_1$-$C_6$-alkyl", "heteroaryl $C_1$-$C_6$-alkyl", "$C_3$-$C_8$-cycloalkyl $C_1$-$C_6$-alkyl" or "heterocycloalkyl $C_1$-$C_6$-alkyl".

"Acyloxy" refers to the group $-OC(O)R$ where R includes H, "$C_1$-$C_6$-alkyl", "$C_2$-$C_6$-alkenyl" "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", "heterocycloalkyl $C_1$-$C_6$-alkyl".

"Alkoxy" refers to the group $-OR$ where R includes "$C_1$-$C_6$-alkyl" or "aryl" or "heteroaryl" or "aryl $C_1$-$C_6$-alkyl" or "heteroaryl $C_1$-$C_6$-alkyl". Particular alkoxy groups include, for example, methoxy, ethoxy, phenoxy and the like.

"Aminocarbonyl" refers to the group $-C(O)NRR^*$ where each R, R* can independently be hydrogen, $C_1$-$C_6$-alkyl, aryl, heteroaryl, "aryl $C_1$-$C_6$-alkyl" or "heteroaryl $C_1$-$C_6$-alkyl". Examples include N-phenyl formamide.

"Acylamino" refers to the group $-NRC(O)R^*$ where R and R* are independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl", "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", or "heterocycloalkyl $C_1$-$C_6$-alkyl".

"Amino" refers to the group —NRR* where each R and R* is independently hydrogen, "$C_1$-$C_6$-alkyl", "aryl", "heteroaryl", "$C_1$-$C_6$-alkyl aryl", "$C_1$-$C_6$-alkyl heteroaryl", "cycloalkyl", or "heterocycloalkyl", and where R and R*, together with the nitrogen atom to which they are attached, can optionally form a 3-8-membered heterocycloalkyl ring.

"Sulfonylamino" refers to a group —NRSO$_2$R* where R and R* are independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cycloalkyl $C_1$-$C_6$-alkyl", or "heterocycloalkyl $C_1$-$C_6$-alkyl".

"Aminosulfonyl" refers to a group —SO$_2$NRR* where R and R* are independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "aryl $C_1$-$C_6$-alkyl" or "heteroaryl $C_1$-$C_6$-alkyl", "aryl $C_2$-$C_6$-alkenyl", "heteroaryl $C_2$-$C_6$-alkenyl", "aryl $C_2$-$C_6$-alkynyl", "heteroaryl $C_2$-$C_6$-alkynyl", "cyclo alkyl $C_1$-$C_6$-alkyl", or "heterocycloalkyl $C_1$-$C_6$-alkyl".

"Sulfonyloxy" refers to a group —OSO$_2$R wherein R is selected from H, "$C_1$-$C_6$-alkyl", "$C_1$-$C_6$-alkyl" optionally substituted with halogens, e.g., an —OSO$_2$—CF$_3$ group, "$C_2$-$C_6$-alkenyl" "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", and "$C_1$-$C_6$-alkyl heterocycloalkyl."

"Sulfonyl" refers to group —SO$_2$R wherein R is selected from H, "aryl", "heteroaryl", "$C_1$-$C_6$-alkyl", "$C_1$-$C_6$-alkyl" substituted with halogens, e.g., an —SO$_2$CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", and "$C_1$-$C_6$-alkyl heterocycloalkyl."

"Sulfinyl" refers to a group —S(O)R wherein R is selected from H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", and "$C_1$-$C_6$-alkyl heterocycloalkyl."

"Sulfanyl" refers to groups —SR where R includes H, "$C_1$-$C_6$-alkyl", "$C_1$-$C_6$-alkyl" optionally substituted with halogens, e.g., a —SCF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", and "$C_1$-$C_6$-alkyl heterocycloalkyl." Particular examples of sulfanyl groups include methylsulfanyl, ethylsulfanyl, and the like.

"Halogen" refers to fluorine, chlorine, bromine and iodine.

"Cyano" refers to —C≡N.

Where a compounds of the present invention (or their prodrugs) has more than one conformation, i.e. a tautomer of an individual compound, both structures are claimed individually and together as mixtures in any ratio. An example of a functional group that commonly tautomerizes is a ketone ←→ enol. Additionally, when a compound of the present invention is depicted as a stereoisomer, enantiomer, cis/trans isomer, and/or conformer, all isomers of the structure are claimed individually and as a mixture in any ratio (e.g., a racemic mixture of enantiomers).

Metabolites of compounds of the present invention are also within the scope of the present invention.

In one embodiment the MEK inhibitor, in particular any of the cited MEK inhibitors inhibits the activity of MEK1 at a concentration of less than 100 μM. In another embodiment the MEK inhibitor inhibits the activity of MEK1 at a concentration of less than 10 μM. In another embodiment the MEK inhibitor inhibits the activity of MEK1 at a concentration of less than 1 μM. In another embodiment the MEK inhibitor inhibits the activity of MEK1 at a concentration of less than 0.1 μM.

The invention relates in a second aspect to a method of treating a mammal suffering from or susceptible to a hyperproliferative disease comprising administering to the mammal a therapeutically effective amount of a compound of Formula (I), a pharmaceutically acceptable salt or a pharmaceutically active derivative thereof.

A hyperproliferative disease may be a cancerous disease including but not limiting to cancer types such as skin (e.g., melanoma), brain, lung, squamous cell, bladder, gastic, pancreatic, breast, head, neck, renal, kidney, ovarian, prostate, colorectal, esophageal, testicular, gynecological or thyroid cancer, or a non cancerous hyperproliferative disease such as benign hyperplasia of the skin (e.g., psoriasis), restenosis, or prostate (e.g., benign prostatic hypertrophy (BPH)).

In one aspect the hyperproliferative disease is related to the hyperactivity of MEK as well as diseases associated with MEK in mammals, or diseases mediated by aberrant cell proliferation, such as cancer or inflammation.

A disease related to the "hyperactivity of MEK" refers to a disease, which can be treated by using any compound according to Formula (I) and which encompasses all diseases in which the upregulation and/or activity of MEK needs to be decreased irrespective of the cause of such disease.

"Pharmaceutically acceptable salts or complexes" refer to salts or complexes of the below-specified compounds of Formula (I). Examples of such salts include, but are not limited to, base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention. Additional examples are salts which are formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, methane sulfonic acid, naphthalene disulfonic acid, and poly-galacturonic acid, as well as salts formed with basic amino acids such as Lysine or Arginine.

A "pharmaceutically active derivative" refers to any compound that upon administration to the recipient, is capable of providing, directly or indirectly, the activity disclosed herein. The term "indirectly" also encompasses prodrugs which may be converted to the active form of the drug via endogenous enzymes or metabolism. Said prodrug is comprised of the active drug compound itself and a chemical masking group. For example, a chemical masking group for alcohol derivatives could be selected from carboxylic acid ester (e.g. acetate, lysine ester) or phosphoric acid esters (e.g. phosphoric acid monoester).

A preferred aspect the invention relates to method of treating a mammal suffering from, or susceptible to, a hyperproliferative disease comprising administering to the mammal a therapeutically effective amount of a compound of Formulae (II), (IIIa), (IIIb), or (IIIc) or a pharmaceutically acceptable salt or a pharmaceutically active derivative thereof. In one aspect of the invention, said hyperproliferative disease is cancer.

The invention also relates to the treatment of a hyperproliferative disease in a mammal that comprises administering to said mammal a therapeutically effective amount of a compound of Formula (I), in combination with an anti-tumor agent selected from the group consisting of mitotic inhibitors, alkylating agents, antimetabolites, intercalating antibiotics, growth factor inhibitors, cell cycle inhibitors, enzyme inhibitors, topoisomerase inhibitors, biological response modifiers, antihormones, angiogenesis inhibitors, and anti-androgens. It is well known in the art which anti-tumor agents are effective in combination therapy. In a preferred aspect, a compound of Formulae (II), (IIIa), (IIIb), or (IIIc) is administered in combination with an anti-tumor agent as described above.

The invention encompasses the use of a MEK inhibitor according to Formula (I) or a pharmaceutically acceptable salt or a pharmaceutically active derivative thereof as a medicament.

In a preferred aspect the invention relates to the use of a compound according to Formulae (II), (IIIa), (IIIb) or (IIIc) or a pharmaceutically acceptable salt or a pharmaceutically active derivative thereof as a medicament.

In one aspect the invention relates to the use of a compound as a medicament, selected from the group of: 6-Fluoro-2-(2-fluoro-4-iodophenylamino)nicotinic acid; (R)—N-((2,2-dimethyl-1,3-dioxolan-4-yl)methoxy)-6-fluoro-2-(2-fluoro-4-iodophenylamino)nicotinamide; (R)—N-(2,3-dihydroxypropoxy)-6-fluoro-2-(2-fluoro-4-iodophenylamino)nicotinamide; 5-Fluoro-3-(2-fluoro-4-iodo-phenylamino)-pyridine-2-carbonitrile; 5-Fluoro-3-(2-fluoro-4-iodo-phenylamino)-pyridine-2-carboxylic acid; 5-Fluoro-3-(2-fluoro-4-iodo-phenylamino)-pyridine-2-carboxylic acid amide; 6-Chloro-3-(2-fluoro-4-iodo-phenylamino)-pyridazine-4-carboxylic acid; 3-(2-Fluoro-4-iodo-phenylamino)-6-morpholin-4-yl-pyridazine-4-carboxylic acid; 3-(2-Fluoro-4-iodo-phenylamino)-6-methoxy-pyridazine-4-carboxylic acid; 6-Chloro-3-(2-fluoro-4-iodo-phenylamino)-pyridazine-4-carboxylic acid (2,2-dimethyl-[1,3]-dioxolan-4-ylmethoxy)-amide; 6-Chloro-3-(2-fluoro-4-iodo-phenylamino)-pyridazine-4-carboxylic acid amide; and 6-Chloro-3-(2-fluoro-4-iodo-phenylamino)-pyridazine-4-carboxylic acid (2-morpholin-4-yl-ethyl)-amide; or pharmaceutically acceptable salts thereof.

The invention also embodies the use of a MEK inhibitor according to Formula (I) or a pharmaceutically acceptable salt or a pharmaceutically active derivative thereof for the preparation of a medicament for the treatment of a hyperproliferative disease. In one aspect, said use relates to the preparation of a medicament for the treatment of cancer.

In a preferred aspect the invention relates to the use of a compound according to Formulae (II), (IIIa), (IIIb) or (IIIc) or a pharmaceutically acceptable salt or a pharmaceutically active derivative thereof for the preparation of a medicament for the treatment of a hyperproliferative disease. In one aspect, said use relates to the preparation of a medicament for the treatment of cancer.

The invention embodies the use of a MEK inhibitor according to Formula (I) or a pharmaceutically acceptable salt or a pharmaceutically active derivative thereof for the treatment of a hyperproliferative disease. In one aspect, said use relates to the treatment of cancer.

In a preferred aspect, the invention relates to the use of a compound according to Formulae (II), (IIIa), (IIIb) or (IIIc) or a pharmaceutically acceptable salt or a pharmaceutically active derivative thereof for the treatment of a hyperproliferative disease. In one aspect, said use relates to the preparation of a medicament for the treatment of cancer.

Furthermore, the invention encompasses pharmaceutical compositions comprising a compound of Formula (I), or a pharmaceutically acceptable salt or a pharmaceutically active derivative thereof, as an active ingredient together with a pharmaceutically acceptable carrier.

In a preferred aspect the invention relates to a pharmaceutical composition comprising a compound of Formulae (II), (IIIa), (IIIb) or (IIIc), or a pharmaceutically acceptable salt or a pharmaceutically active derivative thereof, as an active ingredient, together with a pharmaceutically acceptable carrier.

The present invention also embodies a process for the manufacture of a compound according to Formula (I), said process comprising the step of subjecting an intermediate compound to a coupling reaction shown in Scheme I:

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients, e.g., one or more additional compounds of the present invention, a prodrug compound, or other MEK inhibitor.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compound of Formula (I) can be combined as the active ingredient in admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, suspensions, elixirs and solutions; or carriers such as starches, sugars, microcrystalline cellulose, diluents, granulating agents, lubricants, binders, disintegrating agents and the like in the case of oral solid preparations such as, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of the active compound. The percentage of active compound (a compound of Formulae (I), (II), (IIIa), (IIIb) or (IIIc), a pharmaceutically acceptable salt or composition thereof) in these compositions may, of course, be varied and may conveniently be between about 2 percent to about 60 percent by weight. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds according to Formulae (I), (II), (IIIa), (IIIb) or (IIIc) may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating cancer or other hyperproliferative diseases for which compounds of Formulae (I), (II), (IIIa), (IIIb), or (IIIc) are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

Furthermore, the invention provides in a process for preparing a compound of Formula (I).

In a preferred aspect the invention relates to a method of preparing compounds of Formulae (II), (IIIa), (IIIb), or (IIIc).

The compounds according to Formula (I) can be prepared according to the procedures of the following Schemes and Examples, using appropriate materials and are further exemplified by the following specific examples. Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds according to Formula (I). Those skilled in the art will readily understand that known variations of the conditions and processes of the following preparative procedures can be used to prepare these compounds. The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

An illustration of the preparation of compounds according to Formula (I) is shown in schemes 1-4. Unless otherwise indicated in the schemes, the variables have the same meaning as described above.

Scheme 1

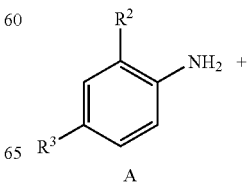

A

-continued

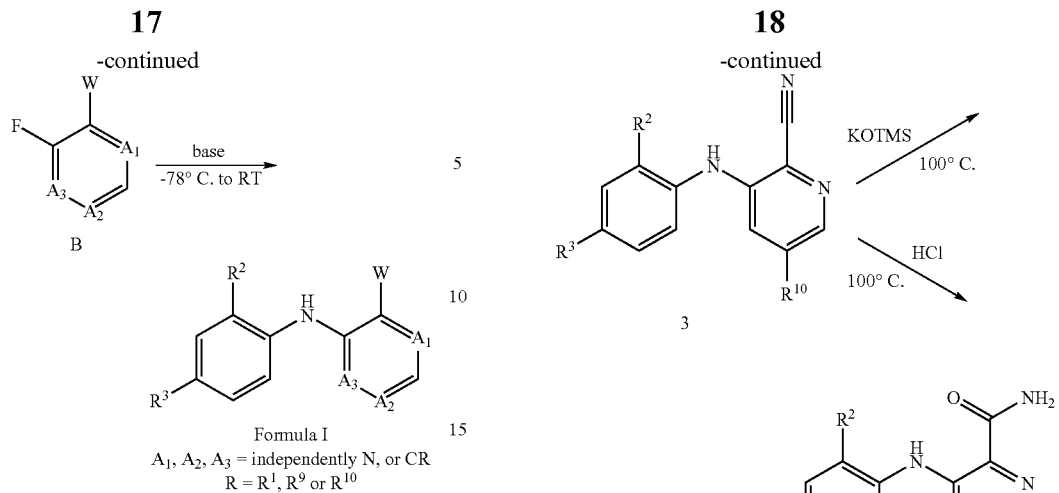

Formula I
A₁, A₂, A₃ = independently N, or CR
R = R¹, R⁹ or R¹⁰ wherein the values of A in ring B are selected from the following: $A_1$ is N, $A_2$ and $A_3$ are both CR; $A_1$ is CR, $A_2$ and $A_3$ are both N; and $A_3$ is N and $A_1$ and $A_2$ are both CR. Values and particular values of $R^2$, $R^3$ and W are as described above.

The process comprises the step of reacting a substituted aniline (A) with a substituted fluoropyridine (B, $A_1$=N and $A_2$=$A_3$=CR; or $A_3$=N and $A_2$=$A_1$=CR), or fluoropyridazine (B, when $A_2$=$A_3$=N and $A_1$=CR). The reaction conditions appropriate for this step include: 1) the dissolution of A and B in a non-reactive solvent, such as THF, DCM, toluene, ether, hexanes; at a temperature range of −100° C. to −20° C., preferably from −90° C. to −50° C.; 2) the addition of a strong, sterically hindered base; 3) and allowing the reaction to go to completion, when the desired product I has been formed. Examples of a base that has appropriate basicity and steric hinderance include, but are not limited to: alkyl-lithium bases; secondary amide bases, and silazide bases. Examples of appropriate bases include, but are not limited to: lithium hexamethyldisilazide (LHMDS); lithium tetramethylpiperidide (LTMP); lithium diisopropylamide (LDA); lithium bis (2-adamantyl)amide; and diisopropylethylamine (DIEA). Bases equivalent to those listed may be ascertained readily by a person skilled in the art. The relative stoichiometric amounts of A and B can be about 1 to 2, preferably about 1 to 1.5 and more preferably about 1 to 1.1, or vice versa. In relation to the limiting reagent, the stoichiometric amount of the base can be about 1 to 4, preferably about 1 to 2, more preferably about 1 to 1.5. One skilled in the art can readily ascertain by well known methods when the reaction has gone to completion, for example by TLC, LC/MS, NMR, etc.

Scheme 1 illustrates the general condensation reaction for the synthesis of compounds of Formula (I). Schemes 2 and 3 illustrate more specific examples of further manipulations of compounds under Formula I of Scheme 1.

Scheme 2

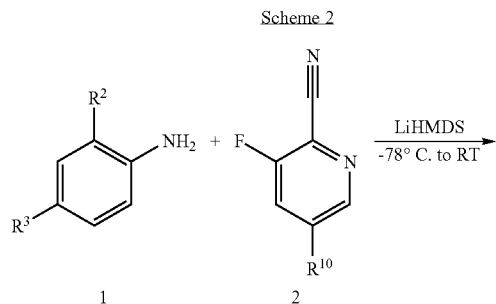

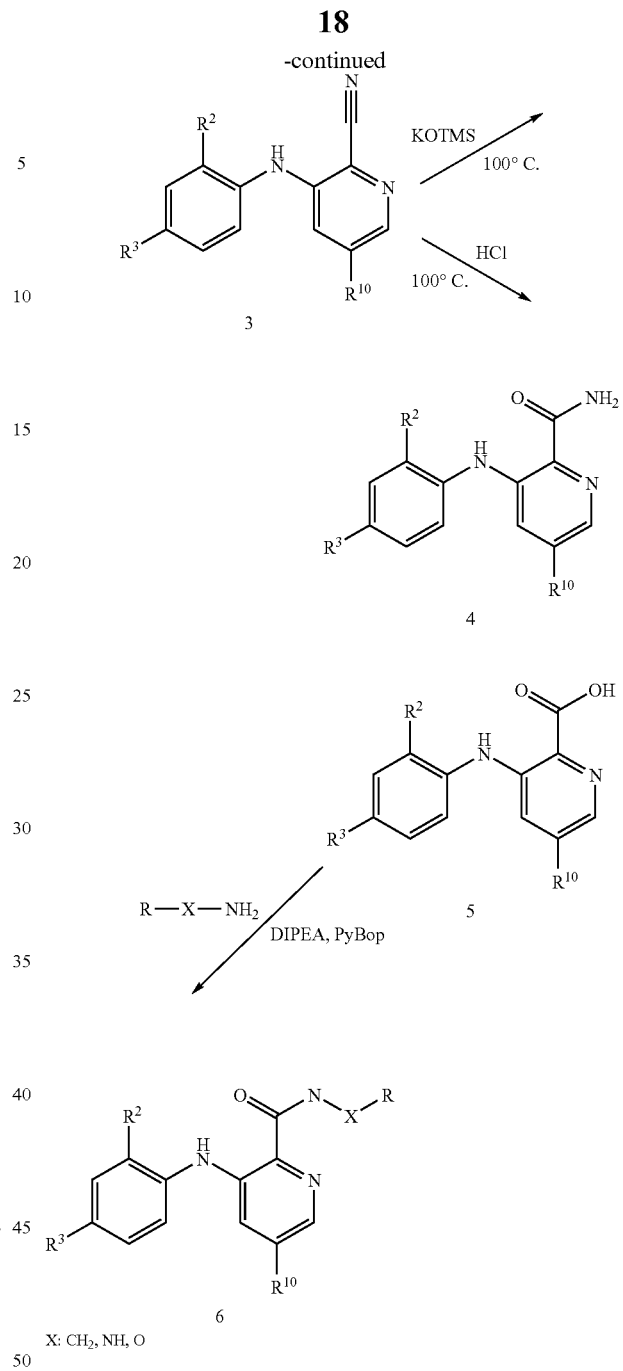

X: CH₂, NH, O

Scheme 2 illustrates the synthesis of examples of derivatives of 3-phenylamino-pyridine-2-carboxylic acid in the present invention. Step 1 is as described for Scheme I above. In step 2 the 3-anilino-pyridine-2-carbonitriles (3) were hydrolysed to the corresponding primary carboxamides (4) (typically by heating in sealed tube with potassium trimethylsilanolate in THF) or to the corresponding carboxylic acids (5) by heating in concentrated hydrochloric acid. The resulting carboxylic acids were converted to various derivatives (6) such as amides, hydrazides, hydroxamic acid esters, etc. by using the corresponding amines, hydrazines, hydroxylamines, etc. and an appropriate coupling reagent including but not limited to PyBOP; CDI, EDC or DCC in a suitable organic solvents, like, for example DMF, THF or DCM. Further manipulations were occasionally employed depending the functionalities of the various R groups.

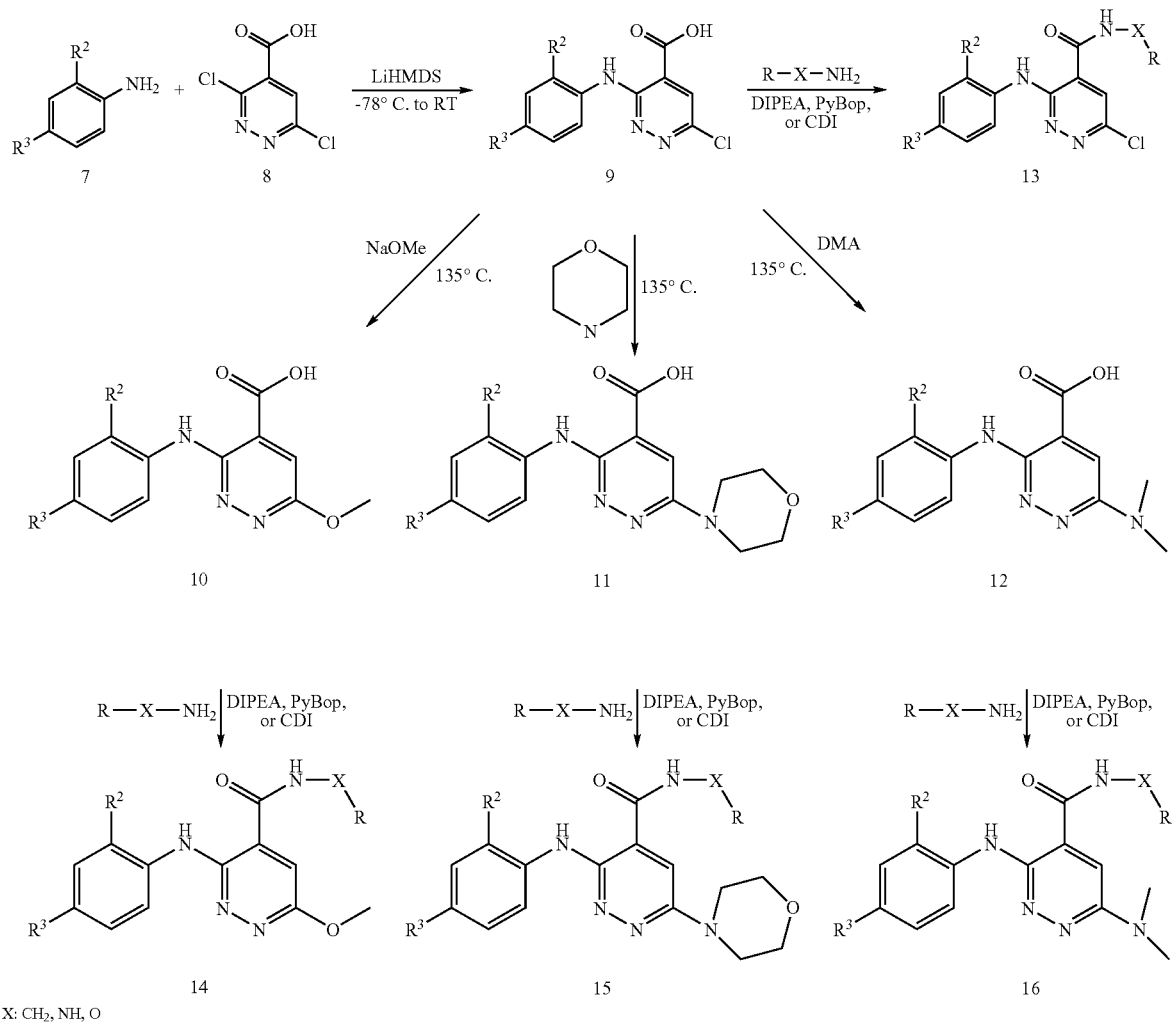

Scheme 3

X: CH₂, NH, O

Scheme 3 illustrates the synthesis of examples of pyridazine derivatives in the present invention. In step 1, the anilines (7) were reacted with 3,6-Dichloro-pyridazine-4-carboxylic acids (8) at −78° C., in an inert solvent, preferable THF, by addition of a base, preferably but not limited to LiHMDS. Next, the resulting 6-Chloro-3-phenylamino-pyridazine-4-carboxylic acids were converted to various derivatives (13) such as amides, hydrazides, hydroxamic acid esters etc. by using the corresponding amines, hydrazines, hydroxylamines etc. and an appropriate coupling reagent including but not limited to PyBOP; CDI, EDC or DCC in a suitable organic solvents, like, for example DMF, THF or DCM. Alternatively 6-Chloro-3-phenylamino-pyridazine-4-carboxylic acids were first derivatized in position 6 (10-12) by substation reactions by heating with various nucleophiles, and subsequently converted to various carboxylic acid derivatives as above (by using the corresponding amines, hydrazines, hydroxylamines etc. and an appropriate coupling reagent including but not limited to PyBOP; CDI, EDC or DCC in a suitable organic solvents, like, for example DMF, THF or DCM). Further manipulations were occasionally employed depending the functionalities of the various R groups.

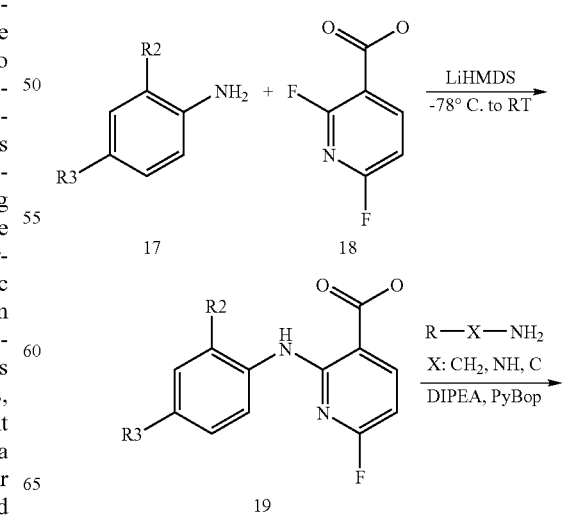

Scheme 4

21
-continued

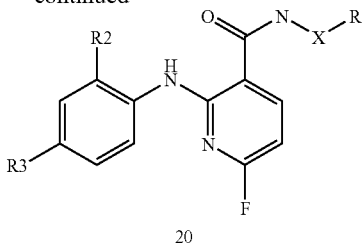

20

Scheme 4 illustrates the synthesis of examples of derivatives of 2-phenylamino-nicotinic acid in the present invention. As described in scheme 1a, in step 1 the anilines (17) were reacted with 2-fluoronicotinic acids (18) at −78° C., in an inert solvent, preferable THF, by addition of a base, preferably but not limited to LiHMDS. The resulting carboxylic acids were converted to various derivatives (20) such as amides, hydrazides, hydroxamic acid esters etc. by using the corresponding amines, hydrazines, hydroxylamines etc. and an appropriate coupling reagent including but not limited to PyBOP; CDI, EDC or DCC in a suitable organic solvents, like, for example DMF, THF or DCM. Further manipulations were occasionally employed depending the functionalities of the various R groups.

Unless otherwise noted, all non-aqueous reactions were carried out either under an argon or nitrogen atmosphere with commercial dry solvents. Compounds were purified using flash column chromatography using Merck silica gel 60 (230-400 mesh). The $^1$H-NMR spectra were recorded on a Joel ECP-400 (400 MHz for $^1$H-NMR) using dimethylsulfoxide or $d_4$-methanol as solvent; chemical shifts are reported in ppm relative to tetramethylsilane.

Analytical Methodology

Analytical LC/MS was performed using the following two methods:

Method A: A Discovery® $C^{18}$, 5 μm, 3×30 mm column was used at a flow rate of 400 μL/min, sample loop 5 μL, mobile phase: (A) methanol with 0.1% formic acid, mobile phase, (B) water with 0.1% formic acid; retention times are given in minutes. Method details: (I) runs on a Quaternary Pump G1311A (Agilent) with UV/Vis diode array detector G1315B (Agilent) and Finnigan LCQ Duo MS detector in ESI+modus with UV-detection at 254 and 280 nm with a gradient of 15-95% (B) in a 3.2 min linear gradient (II) hold for 1.4 min at 95% (B) (III) decrease from 95-15% (B) in a 0.1 min linear gradient (IV) hold for 2.3 min at 15% (B).

Method B: A Waters Symmetry® $C^{18}$, 3.5 μm, 4.6×75 mm column at a flow rate of 400 μL/min, sample loop 5 μL, mobile phase (A) is methanol with 0.1% formic acid, mobile phase (B) is water with 0.1% formic acid; retention times are given in minutes. Methods details: (I) runs on a Binary Pump G1312A (Agilent) with UV/Vis diode array detector G1315B (Agilent) and Applied Biosystems API3000 MS detector in ESI+modus with UV-detection at 254 and 280 nm with a gradient of 20-95% (B) in a 10 min linear gradient (II) hold for 1 min at 95% (B) (III) decrease from 95-20% (B) in a 0.2 min linear gradient (IV) hold for 3.8 min at 20% (B).

If desired, isomers can be separated by methods well known in the art, e.g. by liquid chromatography. Additionally, enantiomers can be separated by methods well known in the art, i.e., by using chiral stationary phase liquid chromatography. Furthermore, enantiomers may be isolated by converting them into diastereomers, i.e. coupling with an enantiomerically pure auxiliary compound, subsequent separation of the resulting diastereomers and cleavage of the auxiliary residue.

22

Alternatively, any enantiomer of a compound of the present invention may be obtained from stereoselective synthesis using optically pure starting materials.

ABBREVIATIONS

Designation
CDI N,N-Carbonyldiimidazole
DCM Dichloromethane
DIPEA N-Ethyldiisopropylamine
DMA Dimethylamine
DMF N,N-Dimethylformamide
EDC 1-(3-Dimethylaminopropyl)-3-ethylcarbodiimide hydrochloride
HPLC High pressure liquid chromatography
LiHMDS Lithium hexamethyldisilazide
NMR Nuclear Magnetic Resonance
PyBOP Benzotriazole-1-yl-oxy-trispyrrolidinophosphonium hexafluorophosphate
tert Tertiary-butyl
THF Tetrahydrofurane
TLC Thin Layer Chromatography
LC/MS Liquid chromatography/Mass spectrometry

REFERENCES

Crews, et al., 258 SCIENCE 478-80 (1992).
Reddy, et al., 22 CANCER METASTASIS REV. 395-403 (2003).
Chang, et al., 17 LEUKEMIA 1263-93 (2003).
Lee, et al., 38 EXP. MOL. MED. 27-35 (2006).
WO 00/42029.
WO 04/056789.
WO 05/051301.
WO 05/000818.

EXAMPLES

The examples presented below are intended to illustrate particular aspects of the invention, and are not intended to limit the scope of the specification or the claims in any way.

Example 1

5-Fluoro-3-(2-fluoro-4-iodo-phenylamino)-pyridine-2-carbonitrile

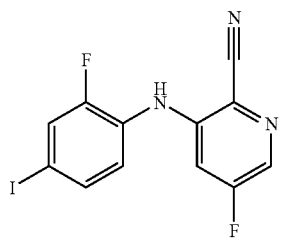 [SMILES: N#Cc1ncc(F)cc1Nc1ccc(I)cc1F]

To solution of 2-fluoro-4-iodoaniline (930.5 mg, 3.93 mmol) and 3,5-difluoropyridine-2-carbonitrile (500 mg, 3.57 mmol) in THF (8 mL) at −78° C., was added LiHMDS (6.1 ml, 7.50 mmol). The mixture was allowed to warm to room temperature and stirred for 12 h. The mixture as diluted with ethyl acetate and washed with $H_2O$ and brine. The organic layer was dried with solid $Na_2SO_4$ and was concentrated. The resulting residue was purified by flash chromatography in silica (25% ethyl acetate-hexane) to give pure product. LC/MS [7.72 min; 358 (M+1)].

Example 2

5-Fluoro-3-(2-fluoro-4-iodo-phenylamino)-pyridine-2-carboxylic acid

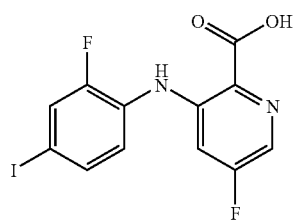 [SMILES: O=C(O)c1ncc(F)cc1Nc1ccc(I)cc1F]

A mixture of 5-fluoro-3-(2-fluoro-4-iodo-phenylamino)-pyridine-2-carbonitrile in concentrated HCl (4 mL, 6N) was heated in sealed tube at 100° C. for 2 days. The mixture was then concentrated and purified by HPLC to afford the pure product. LC/MS [6.89 min; 377 (M+1)].

Example 3

5-Fluoro-3-(2-fluoro-4-iodo-phenylamino)-pyridine-2-carboxylic acid amide

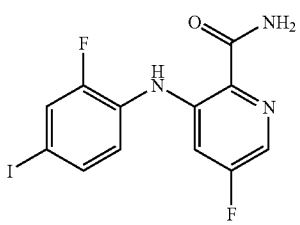 [SMILES: NC(=O)c1ncc(F)cc1Nc1ccc(I)cc1F]

To 5-fluoro-3-(2-fluoro-4-iodo-phenylamino)-pyridine-2-carbonitrile (50 mg, 0.14 mmol) in THF (0.7 mL) was added potassium trimethylsilanolate (40 mg, 0.28 mmol). The mixture was heated in sealed tube at 100° C. overnight. The mixture was then concentrated and purified by HPLC to afford the pure product. LC/MS [6.90 min; 376 (M+1)].

Example 4

6-Chloro-3-(2-fluoro-4-iodo-phenylamino)-pyridazine-4-carboxylic acid

To solution of 2-fluoro-4-iodoaniline (9.21 g, 38.86 mmol) and 3,6-Dichloro-pyridazine-4-carboxylic acid (10.84 g, 64.77 mmol) in THF (80 mL) at −78° C., was added LiHMDS (5 g, 25.91 mmol). The mixture was allowed to warm to room temperature and stirred for 12 h. The mixture as diluted with ethyl acetate and washed with H₂O and brine. The organic layer was dried with solid Na₂SO4 and was concentrated. The resulting residue was purified by flash chromatography in silica (25% ethyl acetate-hexane) to give pure product. LC/MS [4.52 min; 394 (M+1)].

Example 5

3-(2-Fluoro-4-iodo-phenylamino)-6-morpholin-4-yl-pyridazine-4-carboxylic acid

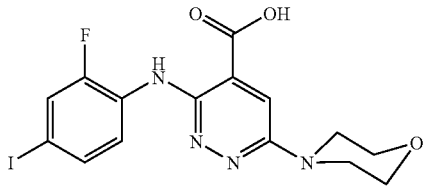 [SMILES: O=C(O)c1cc(N2CCOCC2)nnc1Nc1ccc(I)cc1F]

To mixture of 6-chloro-3-(2-fluoro-4-iodo-phenylamino)-pyridazine-4-carboxylic acid (34 mg, 0.09 mmol) in DMF was added morpholine (37.7 mg, 0.43 mmol). The mixture was heated at 135° C. for 3.5 h. The mixture was diluted with ether and extracted with NaOH (1N). The aqueous layer was acidified by concentrated HCl. The desired product was precipitated and was collected by vacuum filtration. LC/MS [5.51 min; 445 (M+1)].

Example 6

3-(2-Fluoro-4-iodo-phenylamino)-6-methoxy-pyridazine-4-carboxylic acid

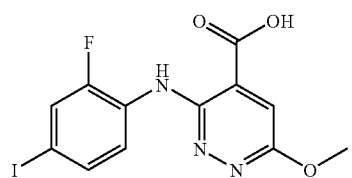 [SMILES: COc1cc(C(=O)O)c(Nc2ccc(I)cc2F)nn1]

To solid 6-chloro-3-(2-fluoro-4-iodo-phenylamino)-pyridazine-4-carboxylic acid (34 mg, 0.09 mmol) in DMF was added NaOMe (0.43 mmol, 0.5 M in MeOH). The mixture was heated at 135° C. for 3 h. The mixture was diluted with ether and extracted with NaOH (1N). The aqueous layer was acidified by concentrated HCl. The desired product was precipitated and was collected by vacuum filtration. LC/MS [8.08 min; 390 (M+1)].

Example 7

6-Chloro-3-(2-fluoro-4-iodo-phenylamino)-pyridazine-4-carboxylic acid (2,2-dimethyl-[1,3]dioxolan-4-ylmethoxy)-amide

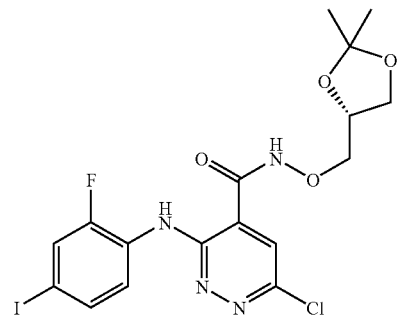 [SMILES: CC1(C)OC[C@H](CONC(=O)c2cc(Cl)nnc2Nc2ccc(I)cc2F)O1]

To a mixture of 6-chloro-3-(2-fluoro-4-iodo-phenylamino)-pyridazine-4-carboxylic acid (46 mg, 0.12 mmol), O-(2,2-dimethyl-[1,3]dioxolan-4-ylmethyl)-hydroxylamine (18.9 mg, 0.13 mmol) and diisopropyl ethylamine (27.2 mg, 0.21 mmol) in dichloromethane, was added PyBop (36.4 mg, 0.06 mmol). The reaction was carried out at room temperature for 5 hours. The mixture was concentrated and purified by flash chromatography to afford the desired adduct. LC/MS [9.50 min; 523 (M+1)].

Example 8

6-Chloro-3-(2-fluoro-4-iodo-phenylamino)-pyridazine-4-carboxylic acid (2,3-dihydroxy-propoxy)-amide

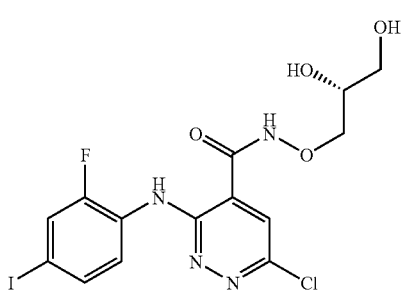 [SMILES: O=C(NOC[C@H](O)CO)c1cc(Cl)nnc1Nc1ccc(I)cc1F]

6-Chloro-N-{[(4R)-2,2-dimethyl-1,3-dioxolan-4-yl]methoxy}-3-[(2-fluoro-4-iodophenyl)amino]pyridazine-4-carboxamide (38 mg, 0.07 mmol) was heated at 90° C. in acetic acid/water (85%, 1.5 mL) for 2 hours. The mixture was concentrated and purified by flash chromatography to give the desired adduct. LC/MS [Method B: rt: 7.02 min; m/z: 483 (M+1)].

Example 9

6-Chloro-3-(2-fluoro-4-iodo-phenylamino)-pyridazine-4-carboxylic acid amide

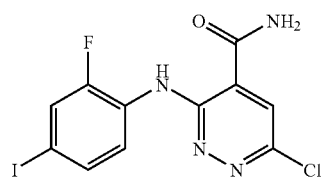 [SMILES: NC(=O)c1cc(Cl)nnc1Nc1ccc(I)cc1F]

6-Chloro-3-[(2-fluoro-4-iodophenyl)amino]pyridazine-4-carboxylic acid (144 mg, 0.37 mmol.) and 1,1'-carbonylbis(1H-imidazole) (119 mg, 0.73 mmol) were suspended in N,N-dimethylformamide (1.00 ml). The mixture was stirred over night (12 hr). Solid ammonium acetate (31 mg, 0.40 mmol) then added. The reaction was stirred for another 5 h. Water (0.5 mL) was then added into the mixture. The desired product was precipitated and was collected by vacuum filtration. LC/MS [7.39 min; 393 (M+1)].

Example 10

6-Chloro-3-(2-fluoro-4-iodo-phenylamino)-pyridazine-4-carboxylic acid (2-morpholin-4-yl-ethyl)-amide

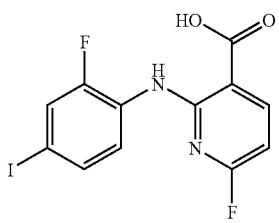 [SMILES: O=C(O)c1ccc(F)nc1Nc1ccc(I)cc1F]

6-chloro-3-[(2-fluoro-4-iodophenyl)amino]pyridazine-4-carboxylic acid (32 mg, 0.08 mmol.) and 1,1'-carbonylbis(1H-imidazole) (15.4 mg, 0.09 mmol) were suspended in N,N-dimethylformamide (0.6 ml). The mixture was stirred over night (12 hr). Morpholine (21.2 mg, 0.16 mmol) was then added. The reaction was stirred for another 5 h. Water (0.5 mL) was then added into the mixture. The desired product was precipitated and was collected by vacuum filtration. LC/MS [4.69 min; 506 (M+1)].

Example 11

6-fluoro-2-[(2-fluoro-4-iodophenyl)amino]nicotinic acid

To solution of 2-fluoro-4-iodoaniline (0.82 g, 3.46 mmol) in THF (10 mL) at −78° C. LiHMDS (6.00 mL, 6.60 mmol) was added. After stirring for 15 min, 2,6-difluoronicotinic acid (0.50 g, 3.14 mmol) was added to the mixture. The mixture was allowed to warm to room temperature until completion. The mixture was washed with NaOH (1 N) and extracted with ether. The aqueous layer was acidified with concentrated HCl and back-extracted with ethyl acetate. The organic layer was concentrated to afford product. Second crop of product was obtained by purifying the THF/ether layer with silica gel chromatography. LC/MS [Method B: rt. 9.09 min, m/z 377 (M+1)].

Example 12

N-{[(4R)-2,2-dimethyl-1,3-dioxolan-4-yl]methoxy}-6-fluoro-2-[(2-fluoro-4-iodophenyl)amino]nicotinamide

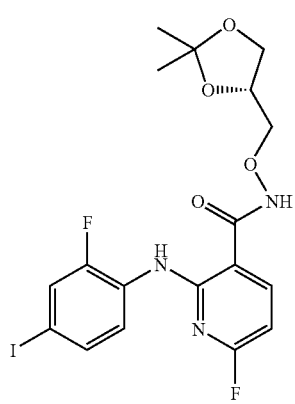 [SMILES: CC1(C)OC[C@H](CONC(=O)c2ccc(F)nc2Nc2ccc(I)cc2F)O1]

The title compound was prepared according the same coupling procedure as Example 7 described above. LC/MS [Method B: rt. 11.11 min, m/z 506 (M+1)].

Example 13

N-[(R)-2,3-Dihydroxy-propoxy]-6-fluoro-2-[(2-fluoro-4-iodo-phenylamino)]-nicotinamide

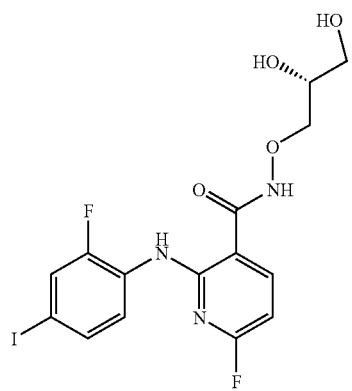 [SMILES: O=C(NOC[C@H](O)CO)c1ccc(F)nc1Nc1ccc(I)cc1F]

The title compound is prepared according the same procedure as Example 8, described above, by deprotection with acid. LC/MS [Method B: rt. 9.74 mM, m/z 466 (M+1)].

Functional Assays

Assay 1: MEK-1 Enzyme Assay (LANCE-HTRF)

Inhibition of human MEK1 kinase activity was monitored with a homogenous, fluorescence-based assay. The assay uses time resolved fluorescence resonance energy transfer to probe for phosphorylation of ERK1 by MEK1. The detailed procedure is described in the following:

Constititutively active MEK-1EE (150 ng/well) and ERK-2K52A (110 ng/well) were incubated in black, 384 well Opti-plates (Perkin Elmer) for 1.5 hrs at room temperature, in the presence of increasing concentrations of inhibitors. The total reaction volume was 50 µl. The inhibitors were serial diluted in kinase buffer (9 µM ATP, 50 mM Tris-HCl pH 8.0, 10 mM $MgCl_2$, 1 mM DTT and 100 µM $Na_3VO_4$), to a final concentration of 1% DMSO. At the end of the incubation, the enzyme reaction was quenched by adding 50 µl of assay buffer containing 50 mM Tris-HCl, 50 mM EDTA, 0.1% BSA and a mixture of 1.25 ug/ml europium labeled anti-phosphotyrosine mAb (Perkin Elmer) and 5 µg/ml of allophycocyanin labeled anti-GST antibody (CIS-US). Plates were agitated on a plate shaker for 30 minutes and the phosphorylation of the ERK-2K52A substrate was measured by homogeneous time resolved fluorescence (HTRF) at 340 nm excitation and 665 nm (Europium)/615 nm (APC) emission filters on the VICTOR V fluorescence plate reader. Phosphorylation is expressed as a ratio of 665 nM signal×10,000/615 nM signal. To assess the inhibitory potential of the compounds, $IC_{50}$-values were determined. Results are shown in Table 1, column 2, where "+++" indicates $IC_{50}$ values below 1 µM, "++" indicates $IC_{50}$ values below 10 µM and above 1 µM, and "+" indicates $IC_{50}$ values above 10 µM.

Assay 2: Tumor Cell Proliferation Assays (ATP Lite)

Murine colon C26 (1500 cells/well), human melanoma A375 (2000 cells/well), or human pancreatic MiaPaCa-2 cells (2000 cells/well) were plated in white, 96 well plates (Corning) in growth media (DMEM with 10% fetal bovine serum, 2 mM glutamine for C26 and MiaPaCa-2, and RPMI with 10% fetal bovine serum, 2 mM glutamine for A375) and cultured overnight at 37° C. in a humidified, 5% $CO_2$ incubator. Inhibitors were serially diluted in 100% DMSO and subsequently added to the cells, in growth media, to reach a final concentration of 0.25% DMSO. The cells were incubated for 4 days in the presence of the test compounds and the proliferation was quantitated using the ATPlite cell proliferation kit (Packard). Results of cell proliferation assay are shown in Table 1. columns 3-5, where "+++" indicates $IC_{50}$ values below 1 µM, "++" indicates $IC_{50}$ values below 10 µM and above 1 µM, and "+" indicates $IC_{50}$ values above 10 µM.

TABLE 1

Results of MEK enzyme assay and tumor cell proliferation assays

| Example | MEK | C26 | A375 | MiaPaCa2 |
|---|---|---|---|---|
| Example 1 | + | | | |
| Example 2 | ++ | | | |
| Example 3 | +++ | + | ++ | + |
| Example 4 | +++ | + | + | + |
| Example 5 | ++ | + | + | + |
| Example 6 | + | + | + | + |
| Example 7 | + | + | + | + |
| Example 8 | + | | | |
| Example 9 | +++ | + | ++ | ++ |
| Example 10 | ++ | | | |
| Example 11 | +++ | + | + | + |
| Example 12 | ++ | | | |
| Example 13 | ++ | + | ++ | + |

What is claimed is:

1. A method of inhibiting MEK in a cancer cell selected from the group consisting of human melanoma cells and human pancreatic cancer cells comprising administering to said cancer cell a therapeutically effective amount of a compound of Formula (I),

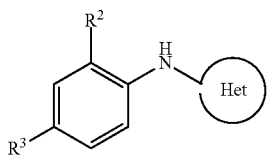

Formula (I)

as well as tautomers, pharmaceutically acceptable salts and pharmaceutically active derivatives thereof, wherein:

Het is selected from

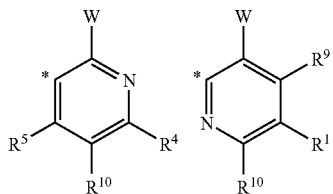

wherein

* is the connecting position;

W is selected from: 1) heteroaryl containing 1-4 heteroatoms or heterocycloalkyl containing 1-4 heteroatoms each of which is optionally substituted by 1 to 5 substituents $R^{11}$; and 2) aryl, halogen, $C_1$-$C_{10}$-alkyl-$OR^6$, $C_1$-$C_{10}$-alkyl-$NR^7R^8$, —C=$NNR^6R^7$, —C=$NOR^7$, $C_1$-$C_{10}$ alkyl($NR^7$)($NR^7R^8$), —C(O)$R^6$, —C(O)$OR^6$, —C(O)$NR^7R^8$, —C(O)$NR^7OR^6$, —C(O)($C_3$-$C_{10}$ cycloalkyl), —C(O)($C_1$-$C_{10}$ alkyl), —C(O)(aryl), —C(O)$NR^7$($C_1$-$C_{10}$ alkyl)heterocycloalkyl, —C(O)(heteroaryl), —C(O)(heterocycloalkyl), —CN, —C(O)$NR^7NR^8R^6$, —C(O)C(O)$R^6$, —$NR^7R^8$, —C(O)$CR^6R^7C(O)R^8$, —$NR^7C(O)R^8$, —NRC(O)$NR^7R^8$ or —C(O)$NR^7NR^8C(O)R^6$;

$R^1$ and $R^9$ are independently selected from: hydrogen, halogen, cyano, azido, $C_1$-$C_6$ alkyl, $C_1$-$C_6$ alkoxy, $C_3$-$C_{10}$ cycloalkyl, aryl, heteroaryl, heterocycloalkyl, $C_1$-$C_4$ alkyl-C(O)$OR^6$, $C_1$-$C_4$ alkyl-$OR^6$, $C_1$-$C_4$ alkyl-C(O)$NR^7R^8$, —C(O)$OR^6$, —C(O)$R^6$, —$NR^7C(O)OR^6$, —OC(O)$R^6$, —$NR^7R^8$, —$SR^6$, and —$NR^7S(O)_2R^6$, wherein said alkyl, aryl, heteroaryl and heterocycloalkyl are substituted or unsubstituted;

$R^2$ and $R^3$ are independently halogen;

$R^4$ and $R^5$ are independently selected from: hydrogen, halogen, $C_1$-$C_6$ alkyl and $C_1$-$C_6$ alkoxy, wherein said alkyl or alkoxy is substituted or unsubstituted;

$R^6$, $R^7$ and $R^8$ are independently selected from: hydrogen, $C_1$-$C_{10}$ alkyl, $C_3$-$C_{10}$ cycloalkyl, aryl, arylalkyl, heteroaryl, heterocycloalkyl, $C_1$-$C_4$ alkyl-C(O)OR', $C_1$-$C_4$ alkyl-OR', $C_1$-$C_4$ alkyl-(heterocycloalkyl), $C_1$-$C_4$ alkyl-diol, and $C_1$-$C_4$ alkyl-C(O)NR'R", wherein said alkyl, cycloalkyl, aryl, heteroaryl and heterocycloalkyl are substituted or unsubstituted; or $R^7$ and $R^8$ can be taken together with the atom to which they are attached to form a 4 to 10 membered heteroaryl or heterocycloalkyl ring, with 1-4 heteroatoms, each of which is substituted or unsubstituted;

$R^{10}$ is selected from hydrogen, halogen or $C_1$-$C_6$ alkyl; wherein said alkyl is substituted or unsubstituted;

$R^{11}$ is selected from: hydrogen, $C_1$-$C_6$-alkyl, —$OR^6$, —$NR^7R^8$, —$SR^6$, and —$NR^7S(O)(O)R'$; and R' and R" are independently selected from hydrogen, $C_1$-$C_6$-alkyl or aryl, wherein said alkyl or aryl is substituted or unsubstituted, wherein said cancer is susceptible to MEK inhibition.

* * * * *